(12) United States Patent
Struck

(10) Patent No.: US 7,122,563 B2
(45) Date of Patent: Oct. 17, 2006

(54) DERIVATIVES OF 4-DEMETHYLPENCLOMEDINE, USE THEREOF AND PREPARATION THEREOF

(75) Inventor: Robert F. Struck, Birmingham, AL (US)

(73) Assignee: Southern Research Institute, Birmingham, AL (US)

( * ) Notice: Subject to any disclaimer, the term of this patent is extended or adjusted under 35 U.S.C. 154(b) by 19 days.

(21) Appl. No.: 11/046,692

(22) Filed: Feb. 1, 2005

(65) Prior Publication Data

US 2006/0173051 A1    Aug. 3, 2006

(51) Int. Cl.
*C07D 213/70*   (2006.01)
*A61K 31/44*   (2006.01)

(52) U.S. Cl. ...................... 514/348; 546/296

(58) Field of Classification Search ............... 514/348; 546/296
See application file for complete search history.

(56) References Cited

U.S. PATENT DOCUMENTS

| | | | | |
|---|---|---|---|---|
| 3,234,228 A | * | 2/1966 | Tomita et al. | 546/302 |
| 3,249,619 A | * | 5/1966 | Johnston | 546/292 |
| 4,717,726 A | | 1/1988 | Tobol | |
| 6,376,518 B1 | | 4/2002 | Struck | |
| 6,391,893 B1 | | 5/2002 | Struck et al. | |

* cited by examiner

*Primary Examiner*—Zinna N. Davis
(74) *Attorney, Agent, or Firm*—Connolly, Bove, Lodge & Hutz, LLP

(57) ABSTRACT

Thiocarbonate and thiocarbamate derivatives of 4-demethylpenclomedine are provided along with pharmaceutical compositions containing them and use for treating cancer. A method for preparing the derivatives is also provided.

19 Claims, No Drawings

DERIVATIVES OF 4-DEMETHYLPENCLOMEDINE, USE THEREOF AND PREPARATION THEREOF

STATEMENT REGARDING FEDERALLY SPONSORED RESEARCH OR DEVELOPMENT

This invention was made using funds provided under Grant No. CA 34200 from the National Cancer Institute of the National Institutes of Health and the U.S. government has certain rights in the invention.

DESCRIPTION

1. Technical Field

The present disclosure relates to certain derivatives of 4-demethylpenclomedine (also referred to herein as DM-PEN) and especially to thiolo- and thiono-carbonate and thiocarbamate derivatives of DM-PEN. The present disclosure also relates to pharmaceutical compositions comprising the disclosed derivatives of 4-demethylpenclomendine, as well as a method of using the compounds in treating cancer in a mammal. The present disclosure also relates to a method for producing the disclosed compounds.

BACKGROUND

Even though significant advances have occurred in treatment of cancer, it still remains a major health concern. It has been reported that cancer is the cause of death of up to one of every four Americans.

Included among the known chemotherapeutic drugs are carmustine, doxorubicin, methotrexate, TAXOL, nitrogen mustard, procarbazine, and vinblastine, to name only a few. However, many chemotherapeutic drugs also produce undesirable side effects in the patient. For example, U.S. Pat. No. 4,717,726 reportedly discloses a compound suitable for inhibiting the growth of certain types of malignant neoplasms in mammals. See also Plowman et al., *Cancer Res.,* 49 (1989), 1909–1915. The disclosed compound, 3,5-dichloro-2,4-dimethoxy-6-(trichloromethyl) pyridine, also known as penclomedine, is not satisfactory as a chemotherapeutic, however, because it is known to produce certain undesirable side effects especially in the central nervous system.

Penclomedine (PEN) was evaluated in Phase I clinical trials at Johns Hopkins University Oncology Center, the University of Wisconsin Comprehensive Cancer Center and Western General Hospital in Edinburgh. Hartman et al. Murine and human in vivo penclomedine metabolism; Clin Cancer Res 2: 953, 1996; O'Reilly et al., Tissue and tumor distribution of $^{14}$C-penclomedine in rats; Clin Cancer Res 2:541; 1996; Berlin et al., Phase I clinical and pharmacokinetic trial of penclomedine using a novel, two-stage trial design for patients with advanced malignancy; J Clin Oncol 16:1142; 1998; O'Reilly et al., Phase I and pharmacologic studies of penclomedine, a novel alkylating agent in patients with solid tumors; J Clin Oncol 15:1974; 1997 and Jodrell et al., Dose-limiting neurotoxicity in a phase I study of penclomedine (NSC 388720, CRC 88-04), a synthetic alpha-picoline derivative, administered intravenously; Brit J Cancer 77: 808; 1998) for possible use in the treatment of breast cancer, based on activity against human breast tumor xenografts and experimental mammary tumor models. Plowman et al., Preclinical antitumor activity of an alpha-picoline derivative, penclomedine (NSC 338720), on human and murine tumors; Cancer Res 49: 1909; 1989; and Harrison et al., Preclinical antitumor activity of penclomedine in mice; cross-resistance, schedule-dependence, and oral activity against tumor xenografts in brain; Cancer Res 51: 1979; 1991) and in the treatment of brain tumors, based on its activity against tumor xenografts in the brain (see Harrison et al; supra).

In all of these clinical trials, dose-limiting neurotoxicity was observed after both intravenous and oral administration and was related to peak plasma levels of PEN (see O'Reilly et al; J. Clin Oncol. 12:1974, supra).

The presence of these toxicities, at much lower peak plasma concentrations compared to those reported in preclinical studies, may preclude the administration of higher doses of penclomedine and the achievement of concentrations associated with optimal antitumor activity. Berlin et al., *Proc. Amer. Assoc. Cancer Res.,* 36, 238 (1005); O'Reilly et al., *Proc. Amer. Soc. Clin. Oncol.,* 14, 471 (1995).

Some relevant background art can be found in O'Reilly et al., *Clinical Cancer Research,* 2 (March 1996), 541–548. This reference describes a study to assess the distribution of $^{14}$C-penclomedine in the tissues and tumors of tumor-bearing rats. The study found that the predominant radioactive species in the brain was penclomedine, which may explain the observed neurotoxicity of the drug.

4-Demethylpenclomedine (DM-PEN) was identified as the major plasma metabolite in patients and rodents (see Hartman et al., Clin Cancer Res. 2:953, supra and O'Reilly et al; Clin Cancer Res. 2:541; supra), and neuroanatomic studies of PEN and DM-PEN in rats revealed cerebellar damage only in the PEN-treated group (see O'Reilly et al, The alkylating agent penclomedine induces degeneration of purkinje cells in the rat cerebellum; Invest New Drugs 21:269; 2003).

3,5-Dichloro-2-methoxy-4-hydroxy-6-(trichloromethyl) pyridine or 4-demethylpenclomdine has been suggested as a compound for treating cancer. See WO 97/46531 to Hartman et al. Also see Waud et al., 4-Demethylpenclomedine, an antitumor-active, potentially normeurotoxic metabolite of penclomedine; Cancer Res, 57:815; 1997.

More recently, a series of acyl derivatives of DM-PEN was prepared and evaluated against MX-1 tumor xenografts, several other human tumor xenografts and murine P388 leukemia, revealing potent activity (see Struck et al; Acyl derivatives of demethylpenclomedine, an antitumor active, normeurotoxic metabolite of penclomedine, Cancer Chemotherap Pharmacol 48:47; 2001; U.S. Pat. No. 6,376,518 to Struck and U.S. Pat. No. 6,391,893 to Struck et al.).

Notwithstanding the advances in cancer treatment that have been made, there still remains room for improved drugs that are effective in treating cancer, while at the same time exhibit reduced adverse side effects.

SUMMARY OF DISCLOSURE

The present disclosure relates to novel derivatives of 4-demethylpenclomedine represented by the following formulae:

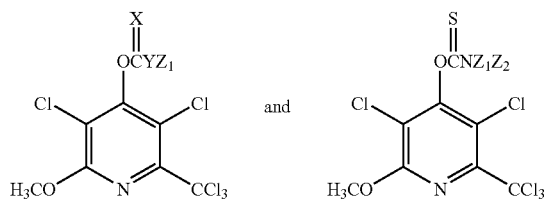 and 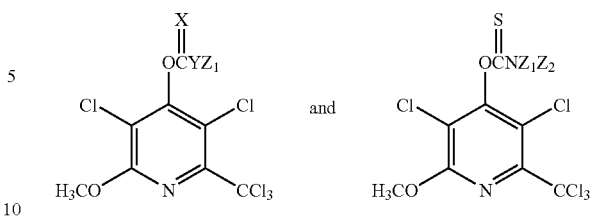

wherein when X is O then Y is S; and when X is S then Y is O or S;

each of $Z_1$ and $Z_2$ is an alkyl having $C_1$–$C_{12}$ or aryl having 6–12 carbon atoms in the ring;

and pharmaceutically acceptable salts thereof.

Another aspect of the present disclosure relates to pharmaceutical compositions containing the above-disclosed compounds. Also disclosed are methods of using the compounds of the present disclosure in treating cancer in a mammal.

A still further aspect of this disclosure is concerned with a method for preparing the above-disclosed compounds.

In particular, the present compounds can be produced by reacting 4-demethylpenclomedine with a compound represented by the formula:

 or or

wherein Hal is halogen, and X and Y are O or S except that both X and Y cannot both be O in the same compound.

If desired, such reaction can be carried out in the presence of a base.

Still other objects and advantages of the present disclosure will become readily apparent by those skilled in the art from the following detailed description, wherein it is shown and described only the preferred embodiments, simply by way of illustration of the best mode. As will be realized, the disclosure is capable of other and different embodiments, and its several details are capable of modifications in various obvious respects, without departing from the disclosure. Accordingly, the description is to be regarded as illustrative in nature and not as restrictive.

Best and Various Modes

The present disclosure is concerned with novel derivatives of 4-demethylpenclomedine compounds represented by the formulae:

wherein when X is O then Y is S; and when X is S then Y is O or S; and each of $Z_1$ and $Z_2$ is an alkyl group containing 1–12 carbon atoms or aryl group containing 6–12 carbon atoms in the ring;

and pharmaceutically acceptable salts thereof.

The alkyl group more typically contains 1–4 carbon atoms. The alkyl groups may be substituted with aprotic moieties such as halo (Cl, F, Br, I), O-alkyl, N(alkyl)$_2$, aralkyl such as benzyl and phenethyl, and heteroaraalkyl containing 1–3 hetero atoms selected from the group of nitrogen, oxygen and sulfur.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted, as well as heteroaryl groups such as pyridyl, imidazolyl, oxazolyl, thiazolyl, isothiazolyl, furyl and thienyl.

Examples of suitable alkyl groups include methyl, ethyl and propyl. Examples of branched alkyl groups include isopropyl and t-butyl. The aryl group is most especially phenyl and an alkyl substituted aromatic group such as phenyl $C_{1-3}$ alkyl and benzyl.

Examples of pharmaceutically acceptable acid addition salts include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, and arylsulfonic, for example p-toluenesulfonic acid.

It has been found according to the present disclosure that the disclosed compounds are surprisingly and advantageously useful in treating mammalian cancer, especially human cancer. The disclosed compounds have been shown to exhibit generally superior activity in comparison to 4-demethylpenclomedine and penclomedine. Moreover, the disclosed compounds are believed to possess reduced toxicity in comparison to both demethylpenclomedine and penclomedine (PEN).

Synthesis of Disclosed Compounds

A general procedure for preparing the above disclosed compounds is as follows: 4-Demethylpenclomedine (DM-PEN) (1 g) in 15 ml dry dichloromethane is treated with a base such as 0.5 ml triethylamine followed by one equivalent of a chlorothiolocarbonate, a chlorothionocarbonate, a chlorodithiocarbonate or thiocarbamoyl chloride, respectively, added dropwise at room temperature in 5 ml dry dichloromethane. The solution is stirred for about 30 min at room temperature and evaporated to dryness via a water aspirator. The residue is triturated with 5 ml acetone and filtered to remove triethylamine hydrochloride. The acetone filtrate is concentrated to 1 ml and separated on an 8 inch, 2 mm silica gel plate containing a fluorescent indicator. The major UV-visible band is eluted with acetone and the solvent evaporated, giving the respective product in high yield. Characterization is provided by mass spectrometry, which reveals the appropriate mass number +1 corresponding to the expected structure, and thin-layer chromatography, which yields a single UV-visible component. Reaction schemes for preparing exemplary compounds of this disclosure are shown below.

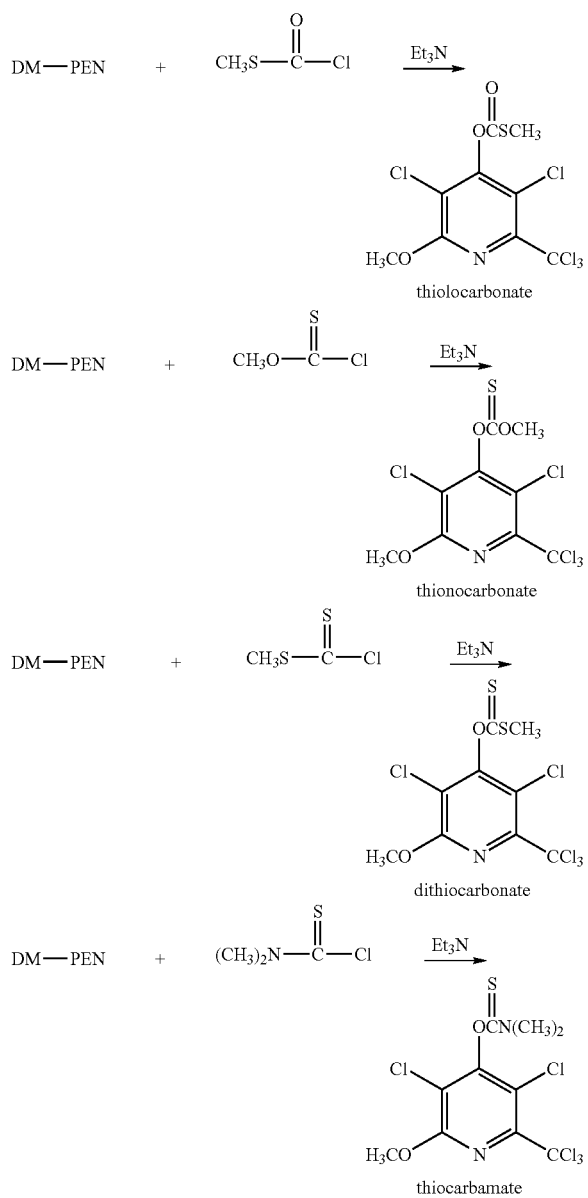

Antitumor Evaluation In Vivo

Antitumor evaluations are conducted as described previously (see Plowman et al; supra and Harrison et al; supra). Athymic NCr-nu/nu and $CD2F_1$ mice are obtained and housed in sterile, filter-capped microisolator cages in a barrier facility. For i.p. injection into mice, DM-PEN and the various derivatives are prepared as a suspension in aqueous hydroxypropyl cellulose. Tumor fragments (30–40 mg) from in vivo passage are implanted into the mammary fat pad of the mice.

Treatment of groups of 5 mice each is initiated when the tumors reach approximately 300 mg in mass and is continued for 5 days for all treatment groups. Each tumor is measured by caliper in two dimensions twice weekly and converted to tumor mass. Antitumor activity is assessed on the basis of tumor growth delay in comparison to a vehicle-treated control, tumor regressions partial and complete), and tumor-free survivors, and experiments are terminated when the control tumors attained a size of 1 gram, which is typically 57–61 days. For i.c. implants, 0.03 ml of an MX-1 tumor brei (containing $10^6$ cells) is implanted into the right hemisphere of the brain of mice.

Treatment of i.c. implants is initiated 1 day after tumor implantation and continued for 5 days. Mice are monitored daily for survival. Antitumor activity is assessed on the basis of the percentage increase in lifespan (ILS) in comparison to a vehicle-treated control, and long-term survivors.

Result

Each derivative is evaluated simultaneously with a DM-PEN control against MX-1 tumor implanted in the mammary fat pad with i.p treatment. A range of dosages of 135, 90 and 60 mg/kg per dose is used, including the maximum tolerated dose. All of the thiolocarbonate derivatives yield superior activity to DM-PEN and produce one or two of five tumor-free survivors. The results are shown in Table 1.

The thionocarbonate and dithiocarbonate derivative, however, yielded only low activity in this tumor model (data not shown).

The methyl thiolocarbonate derivatives of DM-PEN, (DM-SMTC-PEN), is evaluated against intracranially-implanted U251 human glioblastoma xenograft and is observed to be comparably active to the acyl derivatives against this tumor (see Struck et al., supra), DM-SMTC-PEN is also evaluated against intracranially-implanted D54 human glioblastoma multiforme, a highly resistant brain tumor, and yields an increase in life span of 18%, a modest response but one not greatly different from that produced by BCNU, the current drug of choice for clinical treatment of malignant gliomas, the major brain tumor in the U.S.

The antitumor activity of the thiocarbamates is shown in Table 2. Against MX-1 human mammary tumor xenograft, potent antitumor activity greater than that observed for DM-PEN is observed for the dimethyl derivative (DM-DMTC-PEN) and the diethyl derivative (DM-DETC-PEN), with somewhat greater activity being observed for the dimethyl derivative.

Evaluation of DM-DMTC-PEN against intracranially-implanted U251 human brain tumor xenograft for comparison of its activity with that of DM-SMTC-PEN in a side-by-side experiment reveals activity of 44% increase in life span (ILS), which is slightly inferior to DM-SMTC-PEN, which yields and ILS of 56%, but is identical to that of the ethyl and phenyl analogs of DM-SMTC-PEN.

A major concern for the penclomedine (PEN) series of derivatives is their possible neurotoxicity. PEN was removed from clinical development as a potential drug for treating breast cancer because of its dose-limiting neurotoxicity. Consequently, DM-SMTC-PEN is evaluated simultaneously with PEN in a behavioral test of neurotoxicity and is observed to be non-neurotoxic, as indicated by the absence of production of tremors in the DM-SMTC-PEN group in comparison to the PEN group.

TABLE 1

Response of MX-1 Mammary Tumor Implanted in the Mammary Fat Pad to
Treatment with 4-DM-PEN, DM-SETC-PEN, DM-SPTC-PEN and DM-SMTC-PEN

| Agent | IP Dosage (mg/kg/dose) | Schedule | Regressions Partial | Complete | Growth Delay (T-C) | Tumor-free Survivors |
|---|---|---|---|---|---|---|
| 4-DM-PEN | 135 | Days 15–19 | 2 | 0 | 32.8 | 0/5 |
| DM-SETC-PEN | 60 | Days 15–19 | 3 | 2 | >35.2 | 1/5 |
| DM-SPTC-PEN | 135 | Days 15–19 | 2 | 2 | >35.2 | 1/5 |
| DM-SMTC-PEN | 60 | Days 15–19 | 2 | 2 | >41.6 | 2/5 |

Thiolocarbonate Derivatives:
R = methyl - DM - SMTC - PEN
R = ethyl - DM - SETC - PEN
R = phenyl - DM - SPTC - PEN

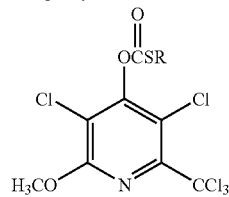

TABLE 2

Response of MX-1 Mammary Tumor Implanted in the Mammary Fat Pad to
Treatment with 4-DM-PEN, DM-DETC-PEN and DM-DMTC-PEN

| Agent | IP Dosage (mg/kg/dose) | Schedule | Regressions Partial | Complete | Growth Delay (T-C) | Tumor-free Survivors |
|---|---|---|---|---|---|---|
| 4-DM-PEN | 135 | Days 15–19 | 2 | 0 | 32.8 | 0/5 |
| DM-DETC-PEN | 135 | Days 15-19 | 1 | 1 | >35.2 | 1/5 |
| DM-DMTC-PEN | 135 | Days 13-17 | 1 | 4 | >37.0 | 3/5 |

Thiocarbamate Derivatives:
R = methyl - DM - DMTC - PEN
R = ethyl - DM - DETC - PEN

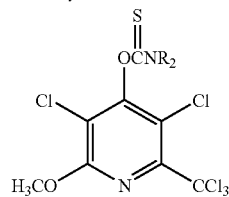

In keeping with the present disclosure, the derivatives of 4-demethylpenclomedine can be used alone or in appropriate association, and also may be used in combination with pharmaceutically acceptable carriers and other pharmaceutically active compounds such as other cancer treatment drugs. The derivatives of 4-demethylpenclomedine also may be used as their acid addition salts. The active agent may be present in the pharmaceutical composition in any suitable quantity.

The pharmaceutically acceptable carriers described herein, for example, vehicles, adjuvants, excipients, or diluents, are well-known to those who are skilled in the art. Typically, the pharmaceutically acceptable carrier is chemically inert to the active compounds and has no detrimental side effects or toxicity under the conditions of use. The pharmaceutically acceptable carriers can include polymers and polymer matrices.

The choice of carrier will be determined in part by the particular method used to administer the composition. Accordingly, there is a wide variety of suitable formulations of the pharmaceutical composition of the present invention. The following formulations for oral, aerosol, parenteral, subcutaneous, intravenous, intraarterial, intramuscular, intraperitoneal, intrathecal, rectal, and vaginal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granule; (c) powders; (d) suspensions in an appropriate liquid; and (e) suitable emulsions. Liquid formulations may include diluents, such as water and alcohols, for example, ethanol, benzyl alcohol, propylene glycol, glycerin, and the polyethylene alcohols, either with or without the addition of a pharmaceutically acceptable surfactant, suspending agent, or emulsifying agent. Capsule forms can be of the ordinary hard-or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, the addition to the active ingredient in an inert base, such as gelatin and glycerin, or sucrose and acadia, emulsions, and gels containing, in addition to the active ingredient, such carriers as are known in the art.

The derivatives of 4-demethylpenclomedine alone or in combination with other suitable components, can be made into aerosol formulations to be administered via inhalation. These aerosol formulations can be placed into pressurized acceptable propellants, such as dichlorodifluoromethane, propane, and nitrogen. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcelluslose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyldialkylammonium halides, and alkylpyridinium halides, (b) anionic detergents such as, for example, alkyl, aryl, and olefin sulfonates, alkyl olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl β-aminopropionates, and 2-alkylimidazoline quaternary ammonium salts, and (e) mixtures thereof.

The parenteral formulations typically contain from about 0.5% to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Pharmaceutically acceptable excipients are also well-known to those who are skilled in the art. The choice of excipient will be determined in part by the particular compound, as well as by the particular method used to administer the composition. Accordingly, there is a wide variety of suitable formulations of the pharmaceutical composition of the present invention. The following methods and excipients are merely exemplary and are in no way limiting. The pharmaceutically acceptable excipients preferably do not interfere with the action of the active ingredients and do not cause adverse side-effects. Suitable carriers and excipients include solvents such as water, alcohol, and propylene glycol, solid absorbants and diluents, surface active agents, suspending agent, tableting binders, lubricants, flavors, and coloring agents.

The formulations can be presented in unit-does or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutical carriers for injectable compositions are well known to those of ordinary skill in the art. See *Pharmaceutics and Pharmacy Practice*, J.B. Lippincott Co., Philadelphia, Pa., Banker and Chalmers, Eds., 238–250 (1982) and *ASHP Handbook on Injectable Drugs*, Toissel, $4^{th}$ ed., 622–630 (1986).

Formulations suitable for topical administration include lozenges comprising the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, and gels containing, in addition to the active ingredient, such carriers as are known in the art.

Additionally, formulations suitable for rectal administration may be presented as suppositories by mixing with a variety of bases such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

One skilled in the art will appreciate that suitable methods of administering a compound of the present invention to an animal are available, and, although more than one route can be used to administer a particular compound, a particular route can provide a more immediate and more effective reaction than another route.

The present disclosure further provides a method of treating cancer in a mammal, especially humans. The method comprises administering an effective treatment amount of a derivative of 4-demethylpenclomedine disclosed above to the mammal.

As regards these applications, the present method includes the administration to an animal, particularly a mammal, and more particularly a human, of a therapeutically effective amount of the compound effective in the inhibition of neoplasia and tumor growth.

The disclosed compounds and compositions can be administered to treat a number of cancers, including leukemias and lymphomas such as acute lymphocytic leukemia, acute nonlymphocytic leukemias, chronic lymphocytic leukemia, chronic myelogenous leukemia, Hodgkin's Disease, non-Hodgkin's lymphomas, and multiple myeloma, childhood solid tumors such as brain tumors, neuroblastoma, retinoblastoma, Wilms Tumor, bone tumors, and soft-tissue sarcomas, common solid tumors of adults such as lung cancer, colon and rectum cancer, breast cancer, prostate cancer, urinary cancers, uterine cancers, oral cancers, pancreatic cancer, melanoma and other skin cancers, stomach cancer, ovarian cancer, brain tumors, liver cancer, laryngeal cancer, thyroid cancer, esophageal cancer, and testicular cancer.

The method disclosed herein is particularly applicable in the treatment of brain, colon, renal, and mammary tumors, and preferably colon, brain and mammary tumors. The method can be practiced on mammals, particularly humans.

The dose administered to an animal, particularly a human, in the context of the present invention should be sufficient to effect a therapeutic response in the animal over a reasonable time frame. One skilled in the art will recognize that dosage will depend upon a variety of factors including the condition of the animal, the body weight of the animal, as well as the severity and stage of the cancer.

A suitable dose is that which will result in a concentration of the active agent in tumor tissue which is known to effect the desired response. The preferred dosage is the amount which results in maximum inhibition of cancer, without unmanageable side effects.

The total amount of the compound of the present disclosure administered in a typical treatment is preferably between about 60 mg/kg and about 2000 mg/kg of body weight for mice, and between about 5 mg/kg and about 100 mg/kg of body weight, and more preferably between 5 mg/kg and about 20 mg/kg of body weight for humans. This total amount is typically, but not necessarily, administered as a series of smaller doses over a period of from about one day to about 24 months, and preferably over a period of 28 days to about 12 months.

The size of the dose also will be determined by the route, timing and frequency of administration as well as the existence, nature and extent of any adverse side effects that might accompany the administration of the compound and the desired physiological effect. It will be appreciated by one of skill in the art that various conditions or disease states, in particular chronic conditions or disease states, may require prolonged treatment involving multiple administrations.

The method disclosed comprises further administering of chemotherapeutic agent other than the derivatives of the present invention. Any suitable chemotherapeutic agent can be employed for this purpose. The chemotherapeutic agent is typically selected from the group consisting of alkylating agents, antimetabolites, natural products, hormonal agents, and miscellaneous agents.

Examples of alkylating chemotherapeutic agents include carmustine, chlorambucil, cisplatin, lomustine, cyclophosphamide, melphalan, mechlorethamine, procarbazine, thiotepa, uracil mustard, triethylenemelamine, busulfan, pipobroman, streptozocin, ifosfamide, dacarbazine, carboplatin, and hexamethylmelamine.

Examples of chemotherapeutic agents that are antimetabolites include cytosine arabinoside, fluorouracil, gemcitabine, hydroxyurea, mercaptopurine, methotrexate, thioguanine, floxuridine, fludarabine, cladribine and L-asparaginase.

Examples of chemotherapeutic agents that are natural products include actinomycin D, bleomycin, camptothecins, daunomycin, doxorubicin, etoposide, mitomycin C, TAXOL (paclitaxel), taxotere, teniposide, vincristine, vinorelbine, idarubicin, MITHRACIN™ (plicamycin), and deoxycoformycin.

An example of hormonal chemotherapeutic agent includes tamoxifen. Examples of the aforesaid miscellaneous chemotherapeutic agents include mitotane, mitoxantrone, vinblastine, and levamisole.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

All publications and patent applications cited in this specification are herein incorporated by reference, and for any and all purposes, as if each individual publication or patent application were specifically and individually indicated to be incorporated by reference.

What is claimed is:

1. A compound represented by the formula:

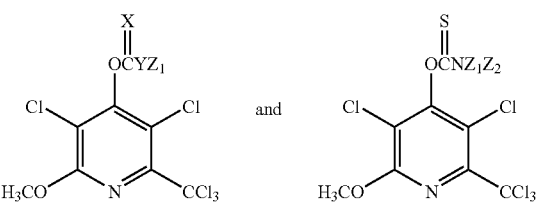

wherein when X is O then Y is S; and when X is S then Y is O or S;

each of $Z_1$ and $Z_2$ is an alkyl having $C_1$–$C_{12}$ or aryl having 6–12 carbon atoms in the ring;

or a pharmaceutically acceptable salt thereof.

2. The compound of claim 1 wherein said alkyl group contains 1–4 carbon atoms.

3. The compound of claim 1 wherein said alkyl group is methyl.

4. The compound of claim 1 being selected from the group consisting of:

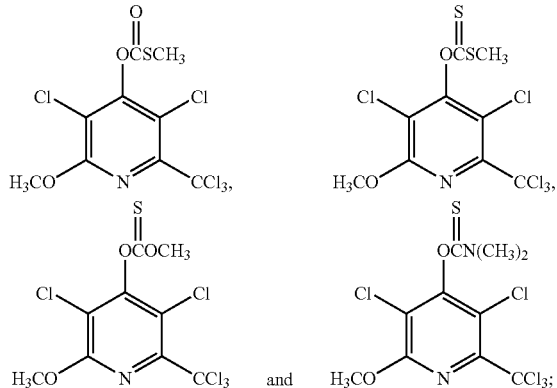

or a pharmaceutically acceptable salt thereof.

5. The compound of claim 1 being represented by the formula:

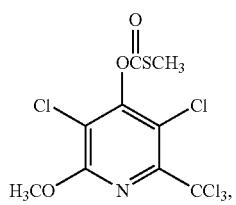

or a pharmaceutically acceptable salt thereof.

6. The compound of claim 1 being represented by the formula:

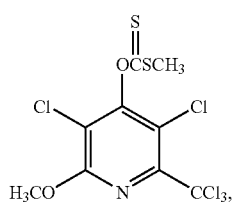

or a pharmaceutically acceptable salt thereof.

7. The compound of claim 1 being represented by the formula:

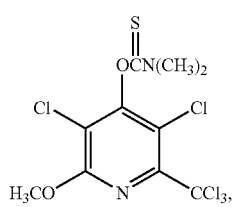

or a pharmaceutically acceptable salt thereof.

8. The compound of claim 1 being represented by the formula:

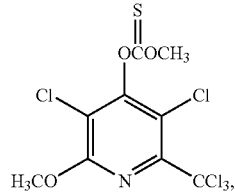

or a pharmaceutically acceptable salt thereof.

9. A pharmaceutical composition comprising a compound of claim 1 and a pharmaceutically acceptable carrier.

10. A method of treating cancer in a mammal comprising administering to the mammal an effective cancer treatment amount of a compound of claim 1.

11. The method of claim 10, wherein the cancer is selected from the group consisting of mammary tumors and brain tumors.

12. The method of claim 10 wherein the treatment amount is from about 5 mg/kg to about 100 mg/kg of the body weight of the mammal.

13. The method of claim 12 wherein the treatment amount is from about 5 mg/kg to about 100 mg/kg of the body weight of the mammal.

14. The method of claim 10 wherein the treatment is carried out over a period of from one day to about 24 months.

15. The method of claim 10 wherein the derivative is administered orally, intravenously or intraperitoneally.

16. The method of claim 10 wherein the mammal is human.

17. A method of producing a compound of claim 1 which comprises reacting 4-demethylpenclomedine with a compound represented by the formula:

or

wherein Hal is halogen, and X and Y are O or S, except that both X and Y cannot be 0 in the same compound.

18. The method of claim 17 wherein Hal is Cl.

19. The method of claim 17 wherein the reacting is carried out in the presence of a base.

* * * * *